(12) United States Patent
Shusterman

(10) Patent No.: US 6,925,324 B2
(45) Date of Patent: Aug. 2, 2005

(54) SYSTEM AND DEVICE FOR MULTI-SCALE ANALYSIS AND REPRESENTATION OF PHYSIOLOGICAL DATA

(76) Inventor: Vladimir Shusterman, 245 Melwood Ave., Apartment 501, Pittsburgh, PA (US) 15213

( * ) Notice: Subject to any disclaimer, the term of this patent is extended or adjusted under 35 U.S.C. 154(b) by 554 days.

(21) Appl. No.: 10/124,651

(22) Filed: Apr. 17, 2002

(65) Prior Publication Data

US 2002/0143263 A1 Oct. 3, 2002

Related U.S. Application Data

(63) Continuation-in-part of application No. 09/583,668, filed on May 30, 2000.

(51) Int. Cl.[7] .............................................. A61B 5/044
(52) U.S. Cl. ..................................................... 600/509
(58) Field of Search .................................. 600/508–521

(56) References Cited

U.S. PATENT DOCUMENTS

| | | | |
|---|---|---|---|
| 4,193,393 A | | 3/1980 | Schlager |
| 4,679,144 A | | 7/1987 | Cox et al. |
| 5,033,475 A | | 7/1991 | Ueda et al. |
| 5,501,229 A | | 3/1996 | Selker et al. |
| 5,724,983 A | | 3/1998 | Selker et al. |
| 5,956,013 A | | 9/1999 | Raj et al. |
| 5,967,995 A | | 10/1999 | Shusterman et al. |
| 6,038,469 A | | 3/2000 | Karlsson et al. |
| 6,389,308 B1 | * | 5/2002 | Shusterman ................ 600/509 |
| 2002/0095259 A1 | * | 7/2002 | Hood et al. ................... 702/19 |

* cited by examiner

*Primary Examiner*—Scott M. Getzow
(74) *Attorney, Agent, or Firm*—David W. Brownlee

(57) ABSTRACT

System comprised of a medical device and method for analyzing physiological and health data and representing the most significant parameters at different levels of detail which are understandable to a lay person and a medical professional. Low, intermediate and high-resolution scales can exchange information between each other for improving the analyses; the scales can be defined according to the corresponding software and hardware resources. A low-resolution Scale I represents a small number of primary elements such as intervals between the heart beats, duration of electrocardiographic PQ, QRS, and QT-intervals, amplitudes of P-, Q-, R-, S-, and T-waves. This real-time analysis is implemented in a portable device that requires minimum computational resources. The set of primary elements and their search criteria can be adjusted using intermediate or high-resolution levels. At the intermediate-resolution Scale II, serial changes in each of the said elements can be determined using a mathematical decomposition into series of basis functions and their coefficients. This scale can be implemented using a specialized processor or a computer organizer. At the high-resolution Scale III, combined serial changes in all primary elements can be determined to provide complete information about the dynamics of the signal. This scale can be implemented using a powerful processor, a network of computers or the Internet. The system can be used for personal or group self-evaluation, emergency or routine ECG analysis, or continuous event, stress-test or bed-side monitoring.

65 Claims, 10 Drawing Sheets

Scale I

| Heart Rate C 63 | Beat U sinus | Axis U 60 | PR-interval U 0.15 | P-amplitude U 0.03 |
|---|---|---|---|---|
| QRS-duration U 0.1 | Q-amplitude U 0.2 | R-amplitude U 0.8 | S-amplitude U 0.2 | T-amplitude U 0.3 |
| ST-segment U 0.0 | QT-interval U 0.4 | | | |

FIG. 4

| Scale I | | | | |
|---|---|---|---|---|
| Heart Rate<br>N<br>67 | Beat<br>N<br>sinus | Axis<br>N<br>50 | PR-interval<br>N<br>0.12 | P-amplitude<br>N<br>0.014 |
| QRS-duration<br>N<br>0.11 | Q-amplitude<br>A<br>0.38 | R-amplitude<br>N<br>1.0 | S-amplitude<br>N<br>0.2 | T-amplitude<br>N<br>0.1 |
| ST-segment<br>N<br>0.0 | QT-interval<br>A<br>0.58 | | | |

| Scale I | | | | |
|---|---|---|---|---|
| Heart Rate<br>U<br>67 | Beat<br>U<br>sinus | Axis<br>U<br>50 | PR-interval<br>U<br>0.12 | P-amplitude<br>U<br>0.014 |
| QRS-duration<br>U<br>0.11 | Q-amplitude<br>U<br>0.38 | R-amplitude<br>U<br>1.0 | S-amplitude<br>U<br>0.2 | T-amplitude<br>C<br>-0.35 |
| ST-segment<br>C<br>-0.02 | QT-interval<br>U<br>0.58 | | | |

FIG. 10

SYSTEM AND DEVICE FOR MULTI-SCALE ANALYSIS AND REPRESENTATION OF PHYSIOLOGICAL DATA

CROSS-REFERENCE TO RELATED APPLICATION

This is a continuation-in-part of application Ser. No. 09/583,668, filed May 30, 2000.

FIELD OF THE INVENTION

This invention relates to the field of a method and apparatus for analyzing physiological data and its serial changes, including small changes that cannot be exposed by conventional analysis, structuring and representing the results in the form understandable both to lay public and medical professionals.

BACKGROUND OF THE INVENTION

Electrocardiogram is one of the most common medical examinations of cardiac electrical activity, which is performed by a medical professional or paramedics. Registration of ECG is relatively simple, however, its analysis requires a highly qualified physician with substantial experience in electrocardiography.

In general, there are two types of ECG tests, a one-time recording during a few seconds and a long-term monitoring which can be performed during various physiological tests, regular daily activities or as a round-the-clock monitoring in patients with serious medical disturbances. Each test requires a specialized protocol for registering and analyzing ECG signals.

One-time ECG recording is usually performed by ECG technicians or paramedics. The recording then is transferred to a physician for analysis, which includes a number of procedures. First, the cardiac complexes are visually identified by their characteristic shape consisting of a sequence of the following waves: P-, Q-, R-, S-, T- and sometimes U-wave. Next, these complexes are classified according to their origin as normal or sinus, supraventricular, ventricular complexes and their subtypes. The distance between two consecutive complexes is measured to determine the heart rate. Next, a number of the most important parameters including the amplitudes of each wave, the duration of PQ, QRS, and QT-intervals, and the amplitude of ST-segment are measured. Finally, the signals are compared with the recordings that were previously obtained from the same patients to determine serial changes in cardiac electrical activity.

Comparison of serial recordings is an important part of standard ECG examination that allows detection of changes and determining their time course. The comparison is performed visually by an experienced medical professional. The accuracy of this subjective comparison is not high and varies among physicians. The accuracy is not stable even in the same physician when the same measurements are repeated several times.

There are a number of prior art computerized systems that follow these basic steps of analysis and measure characteristic waves of ECG and prepare preliminary report for physicians. Since the number of analyzed variables and their combinations is large, these systems use sophisticated processing algorithms that require fast and powerful microprocessors or computers with a large memory available for processing.

Systems for long-term monitoring consist of two types, recording and real-time systems. Recording systems include 24-hour Holter monitors and event monitors, which record the data after a manual signal (event). Processing of these recordings, which include a large amount of data, consists of computer-assisted scanning with subsequent manual verification by an experienced medical professional. The results of analysis which include average heart rates, number of normal and types of abnormal beats during different periods of time, are submitted to a physician for final verification and conclusion.

Real-time systems include event-monitors, bedside monitors, stress-test systems and other devices for monitoring 1–2 critically important parameters and generating alarm or presenting the output information on a monitor. These systems perform an incomplete examination tracking the changes in heart rate and sometimes changes in the ST-segment. While this information is important for real-time control of a test or treatment, a number of important ECG changes, including changes in Q-, T-, or P-wave amplitude, QT-duration, are not exposed by this analysis.

It is known to provide portable ECG monitors that will sound an alarm or other signal to alert the user or an attendant of abnormal or unusual changes in the waveforms of the ECG signal. Such devices are, for example, disclosed in U.S. Pat. Nos. 4,193,393; 4,679,144; 5,033,475; 5,501,229 and 5,724,983. A system is also known, from U.S. Pat. No. 6,038,469, that includes at least one monitoring module for receiving ECG signals, a circuit for analyzing the signal, a plurality of parameters related to a patient's ischemic condition, and a network for exchanging data with a central unit, either by hard wire or telemetry. The monitor can be used in an ambulatory application in which the ECG signals are recorded and later sent to a central processing unit or units, which may be capable of sending information and data to the portable unit(s).

Shusterman et al. U.S. Pat. No. 5,967,995 has identified small cumulative changes in the series of cardiac inter-beat intervals using the Principal Component Analysis (PCA). This method accurately identified unstable dynamics of cardiac rhythm and predicted cardiac arrhythmias as early as several hours before the event when all known physiological indicators remained normal. The Shusterman et al. invention further extends the applications of PCA to the ECG signal.

SUMMARY OF THE INVENTION

This invention provides a portable and easy-to-use system for structured and complete analysis and representation of electrocardiogram and its serial changes quantitatively for medical professionals and qualitatively for a lay patient who does not have any medical background. Structuring of the analysis is achieved by constructing the at least two, and preferably three, information scales that represent the most significant parameters at different level of detail. In addition to the ECG, the multi-scale analysis and representation can be applied to other physiological data that include but are not limited to blood pressure, cardiac output, vascular activity, temperature, respiration, cardiac, abdominal, or breathing sounds, blood flow, hormonal concentration, neural activity, electroencephalographic activity, and other electrical, mechanic, sonic, biochemical, and biophysical processes in the human body. This multi-scale analysis and representation can also be applied to other information related to human life, including demographic (age, gender), environmental (pollution, job conditions), and psychological data. The values of the data obtained from individual patients can be compared with the average values obtained in a group or a population of patients to facilitate analysis of individual data and to determine the values that characterize groups of patients with similar characteristics and/or similar disorders.

Low, intermediate and high-resolution scales are defined according to the corresponding software and hardware resources. A low-resolution (Scale I) represents a small number of the most important primary elements such as intervals between the heart beats, duration of PQ, QRS, and QT-intervals, amplitudes of P-, Q-, R-, S-, and T-waves. This real-time analysis is implemented in a portable device that requires minimum computational resources. The set of primary elements and their search criteria are adjusted for each ECG utilizing computational resources of intermediate or high-resolution levels. At the intermediate-resolution (Scale II), serial changes in each of the said elements are determined using a mathematical decomposition into series of orthogonal basis functions and their coefficients. This scale is implemented using a specialized processor or a computer organizer. At the high-resolution (Scale III), serial changes in all elements of the ECG and their combinations are extracted using orthogonal mathematical decomposition to provide complete information about the dynamics of the signal. This scale is implemented using a powerful processor, a network of computers or the Internet.

Scale I may be implemented in a portable, pocket-size device, in which the signal is decomposed into a plurality of primary elements and parameters such as intervals between the heart beats, type of a cardiac complex, amplitudes and duration of P-, QRS, T-, and U-wave, QT-interval, amplitude of ST-segment. Scale I of the system provides the means for real-time electrocardiographic analysis by comparing the primary elements of ECG with reference values (individual thresholds) using the minimum computational resources. The reference values are programmed into the device based on normal values for the primary elements for the patient. Scale I includes means for adjustment of individual thresholds and criteria for rejection of noisy data. A detector of noise and error rejects the noisy data if the primary elements exceed physiologic range. Alternatively, modification of the primary elements and adjustment of their search criteria can be performed automatically at the higher-resolution Scale II or Scale III. In this case, the Scale I analysis is implemented using a programmable microprocessor that can be re-programmed at the higher-resolution scales to account for the individual characteristics of the ECG pattern and monitoring goals. Specific sets of primary elements can be used for patients with different cardiovascular abnormalities.

Scale I can be used in two modes: static mode and dynamic mode. The static mode is used for one-time ECG examination in which the newly acquired primary elements are compared with the default reference values. The dynamic mode is used for comparison of the newly acquired primary elements and waveforms with the primary elements and waveforms that were previously acquired from the same person. The shapes of QRS, T, and P-waves are compared using cross-correlation function. A small magnitude of the difference between the two measurements permits classifying them as substantially similar and keeping only one measurement in the memory.

Scale I provides sufficient information for standard, one-time, clinical ECG examination. The most significant primary elements may be represented as a color, symbol, or other easy-to-read encoding of indicators that make the results useful and understandable for a lay person and a medical professional. Each signal-indicator corresponds to a single primary element. In the static mode, the values of the indicators are preferably color-coded for a lay person into normal, moderately or severely abnormal. This representation constitutes a static screen. Alternatively, the indicators may be symbol-coded, N for normal and A for abnormal reading; they may vibrate or produce a sound output for people with vision or hearing impairments. For a medical professional, the indicators provide exact, quantitative values of the primary elements. In the dynamic mode, the indicators are preferably symbol (or color)-coded into C for changed or U for unchanged. This representation constitutes a dynamic screen.

Intermediate-resolution Scale II allows viewing the ECG with automatically determined primary elements on a display and interactive editing of the set of primary elements and their search criteria. The editing can be performed by a user or a medical professional to modify the set of characteristic points or to adjust their search criteria, and can be performed either manually or automatically by the software. The individually adjusted search criteria can then be used to re-program the Scale I analysis as described earlier.

Scale II allows accurate comparison of serial ECGs and detection of small serial changes that may be unexposed by visual inspection of the signals. This scale requires higher computational resources than Scale I and can be implemented in a specialized processor, computer organizer or a personal computer. These computational resources also allow manual entering text information about the patient into the database and specific instructions regarding adjustment of time windows, threshold values, and other variables. To perform the Scale II analysis, the primary elements from serial ECGs are stored into a database to construct the time series for each primary element. The series is decomposed into a few most significant basis functions and coefficients using Principal Component Analysis (PCA) or any other orthogonal set of basis functions. The newly acquired values of the primary elements are compared with the series of the previously obtained values. Furthermore, the changes in the series of PCA coefficients are analyzed to detect small cumulative changes in the dynamics of the series that indicate instability in the cardiac electrical activity.

High-resolution Scale III is used to analyze individual and combined changes in the primary elements; at this scale, the number of the primary variables is increased to include the entire waveform of the cardiac complexes. This allows the most sensitive and accurate detection of the small changes in the individual electrocardiographic pattern. The same PCA approach is used at this scale to expose small serial changes in the ECG recordings. Scale III requires higher computational resources compared to Scale I and Scale II; it may be implemented in a powerful processing unit such as a personal or specialized computer or a distributed network of computers or the Internet.

Systems and analysis units made in accordance with this invention preferably include software and devices for exchanging information and data between the low resolution analysis modules or units and higher resolution modules or units in order to improve the functionality of the analysis. Such improved functionality can be in accuracy, efficiency, speed, usefulness or meaningfulness of the analysis. The exchange of data can also include instructions from a higher level analysis unit to a lower level analysis unit to adjust the analysis or select different primary elements to be analyzed.

This invention can be used for one-time examinations by patients, medical professionals, paramedics and lay public, and for dynamic assessment of changes in cardiac electrical activity. The information can be transmitted to an external computer system or a network of computers. For a lay person, the system may also include a database explaining significance of the changes in each primary element and providing simple recommendations about the measures that has to be taken if the readings of the indicators become abnormal. These may include complete cessation of physical activity, contacting a medical professional, taking a medication, etc. More detailed recommendations might be provided for patients who have specific abnormalities or medications. These patients might require special monitoring or individual adjustment of their primary elements. For example, specific monitoring the duration of QT-interval is important in patients taking antiarrhythmic drugs that prolong QT-interval.

The system can be used as first-aid ECG analyzer for emergency units, paramedics, and medical personnel;

ECG analyzer for a routine medical examination;

a personal one-time or serial ECG analyzer with storage of individual electrocardiographic historic data, adaptive adjustment of individual thresholds and assessment of changes in individual ECG pattern;

a one-time or serial ECG analyzer for a group of people, a family or a patient group, with storage of individual electrocardiographic historic data for each person, adjustment of individual thresholds and assessment of changes in individual ECG patterns;

event-monitoring device including patient-detected events, changes in heart rate or ST-segment;

arrhythmia, bed-side, stress-test monitoring;

pacemaker and other implantable device checking;

evaluation of the treatment efficacy, side effects and progression of the disease.

The multi-scale analysis and representation can be applied for improved detection of changes during one-time examination, for assessement of short term and long term dynamics, which include fitness level, disease progression, treatment and side effects control, physical examination, early detection of subtle changes, and timely initiation or correction of therapy, early prediction and prevention of physiological disorders and abnormalities.

Accordingly, an object of this invention is to provide a system for analyzing ECG and/or other physiological data at least at two levels of detail or resolution. Both levels of resolution are presented in simple representation that can be understood by lay persons, as well as medical professionals.

A further object of this invention is to provide an ECG analyzing system that includes a monitoring device for receiving and analyzing ECG signals and which includes means for communicating with an external computer to which the ECG signals can be forwarded for more complex analysis. The monitoring device can be reprogrammed by the external computer to select the primary elements of the ECG signals that are unstable or abnormal. The low level analysis performed by the monitoring device is thus focused on the critical primary elements for that patient.

The above and other objects and advantages of this invention will be more fully understood and appreciated by reference to the following description and the drawings.

BRIEF DESCRIPTION OF THE DRAWINGS

A full understanding of the invention can be gained from the following description of the preferred embodiments when read in conjunction with the accompanying drawings in which:

FIG. 4 shows the set of output indicators that represent the results of ECG analysis at Scale I both qualitatively and quantitatively in a dynamic mode ("U" represents unchanged value and "C" represents a changed value of a characteristic parameter compared to a previous recording).

FIG. 10 shows the readings from the indicators at Scale I in the dynamic mode for the abnormal ECG in FIG. 9.

DESCRIPTION OF THE PREFERRED EMBODIMENTS

Figure 1:
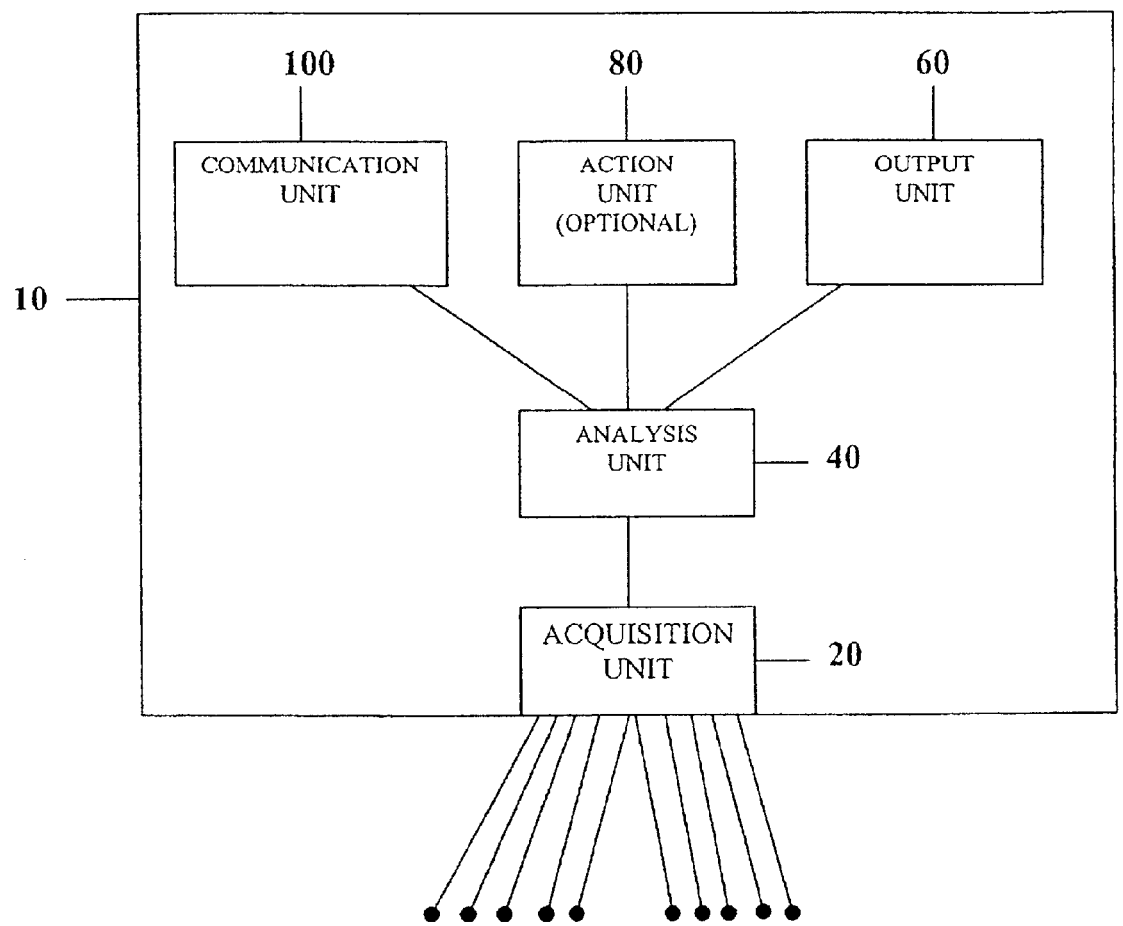
FIG. 1 is a block diagram of the medical device of the preferred embodiment of this invention.
Figure 2:
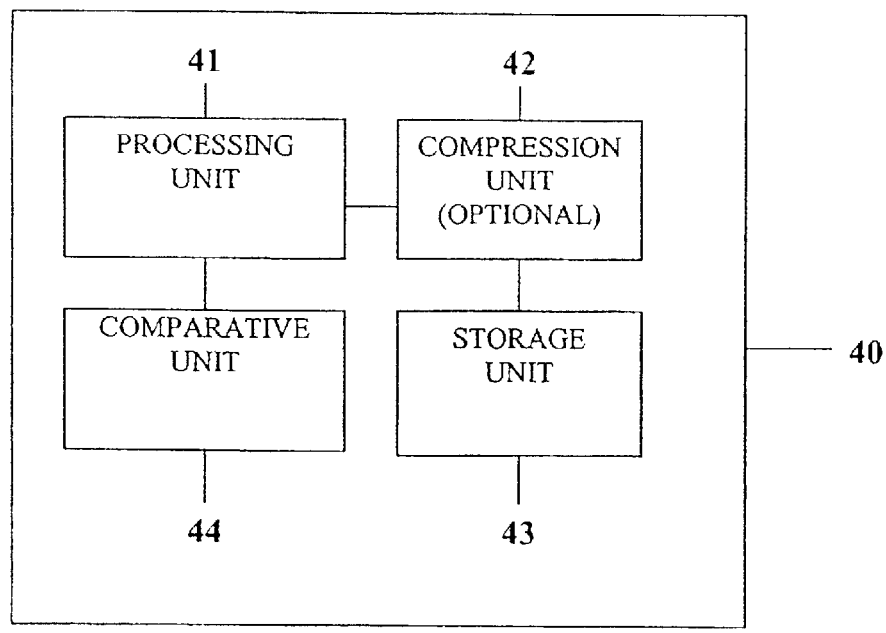
FIG. 2 is a block diagram of the analysis unit from FIG. 1.

FIG. 1 is a block-diagram of a preferred embodiment of a medical device 10 of this invention. The device consists of an acquisition unit 20 that may have several electrodes 25 for attachment to a patient, not shown, to receive electrocardiographic and/or other physiological data, an analysis unit 40, an optional output unit 60, an action unit 80 and a communication unit 100. Standard ECG recorders having acquisition units and storage units are available from several companies such as Hewlett-Packard (Model 1700A) and GE Marquette Medical systems (Mac 500). Portable ECG monitors that record and store segments of ECG are available from Integrated Medical Devices (Model 1200). The acquisition part may receive ECG data from a recorded data source for analysis, but preferably receives the data real-time, on-line through the electrodes 25 that are connected to a patient. As used herein, patient means an animal, and most likely a human. The medical device further includes an analysis unit or module 40 which, in turn, consists of processing, compression, storage, and comparison units (FIG. 2). The processing unit 41 can be a typical computer or personal computer of the type available from many vendors such as IBM and Hewlett-Packard. The processing unit 41 is programmed to detect a plurality of characteristic points such as the onset, peak and offset of P-, Q-, R-, S-, T-, U-waves, and computes the characteristic parameters or primary elements which include amplitudes of the said waves and ST-segment, duration of PQ-, QRS-, and QT-intervals. The processing unit 41 has a programmable microprocessor that can be programmed to modify or change the set of primary elements or to adjust their search criteria. This allows individual adjustment of the characteristic points which, in turn, increases the accuracy of detection of the primary elements. For instance, in signals with biphasic T-wave, two T-peaks should be detected, whereas monophasic T-wave requires detection of a single T-peak. Furthermore, the criteria for determining the offset of biphasic T-wave are different from the criteria for the offset of monophasic T-wave. Individual adjustment of the primary elements and their search criteria increases the accuracy of the detection of characteristic points in different ECG patterns. Still another possibility is analysis of combined changes in some primary elements or disabling analysis of the other elements. For example, in patients with possible electrolyte abnormalities, the amplitudes of the T-wave and U-wave may be combined into a single index which will be convenient for monitoring. Furthermore, the set of monitored primary elements can be modified according to the specifics of cardiovascular abnormality. For example, in patients with coronary artery disease, the amplitude and the slope of the ST-segment should be monitored continuously.

Figure 3:
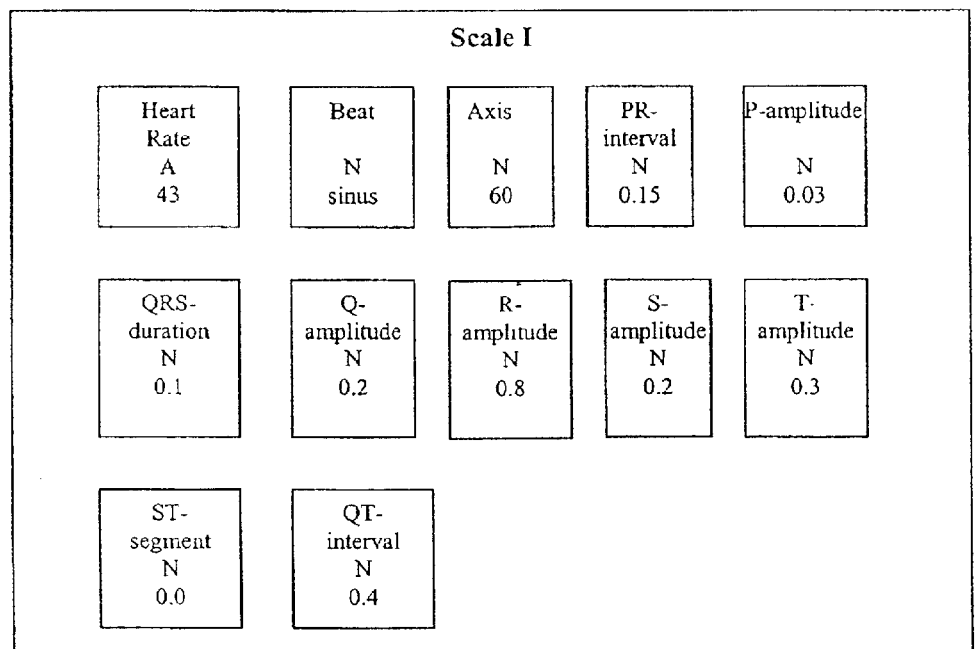
FIG. 3 shows the set of indicators that represent the results of ECG analysis at Scale I both qualitatively and quantitatively in a static mode ("N" denotes normal value and "A" denotes an abnormal value of a characteristic parameter).

Compression unit 42 compresses the ECG waveform into a few weighted basis vectors and their coefficients using principal component analysis, wavelet decomposition, or other orthogonal mathematical transformation. Storage unit 43 stores the compressed waveforms and the computed primary elements into memory. Comparative unit 44 compares the newly acquired waveforms and newly computed primary elements with the waveforms and primary elements previously stored in the storage unit 43. The analysis unit 40 has means for adjusting the thresholds for each indicator, whereas the default values correspond to normal ECG. An output unit 60 includes a screen or a set of indicators for displaying the ECG waveforms and the computed primary elements in comparison with the previously stored primary elements or in comparison with the default reference values. The results of comparison can be represented both qualitatively and quantitatively in the dynamic and static modes. In the static mode, the quantitative representation includes exact values of the primary elements and the type of the cardiac complexes, whereas the qualitative representation includes indication of each parameter as being normal (N) or abnormal (A) as shown in FIG. 3. Abnormal readings may be further classified into moderately abnormal and severely abnormal. To make the indicators understandable to a lay person, the degree of abnormality may be color-coded: green color corresponds to a normal value, yellow corresponds to a moderate abnormality, and red corresponds to a severe abnormality. In the dynamic mode, the quantitative representation shows the differences between the newly acquired and stored primary elements and waveforns, whereas the qualitative representation includes indication of each parameter as being changed (C) or unchanged (U) as shown in FIG. 4. The output unit 60 may alternatively or additionally feed an output data to an action unit 80 for sounding an alarm, generating a vibration, or taking appropriate measures, such as applying the drugs or adjusting the therapy mode. Communication unit 100 transmits the information between the device 10 and external higher-level processing device 150. The communication unit 100 may be a modem or a wireless transmitter/receiver. Electrocardiographic signals and recorded values of primary elements and indexes are transmitted from the device 10 to higher level devices for more detailed processing and storage. The higher-level device 110 preferably transmits back to device 10 a set of primary elements and their search criteria to be used in device 10.

Figure 5:
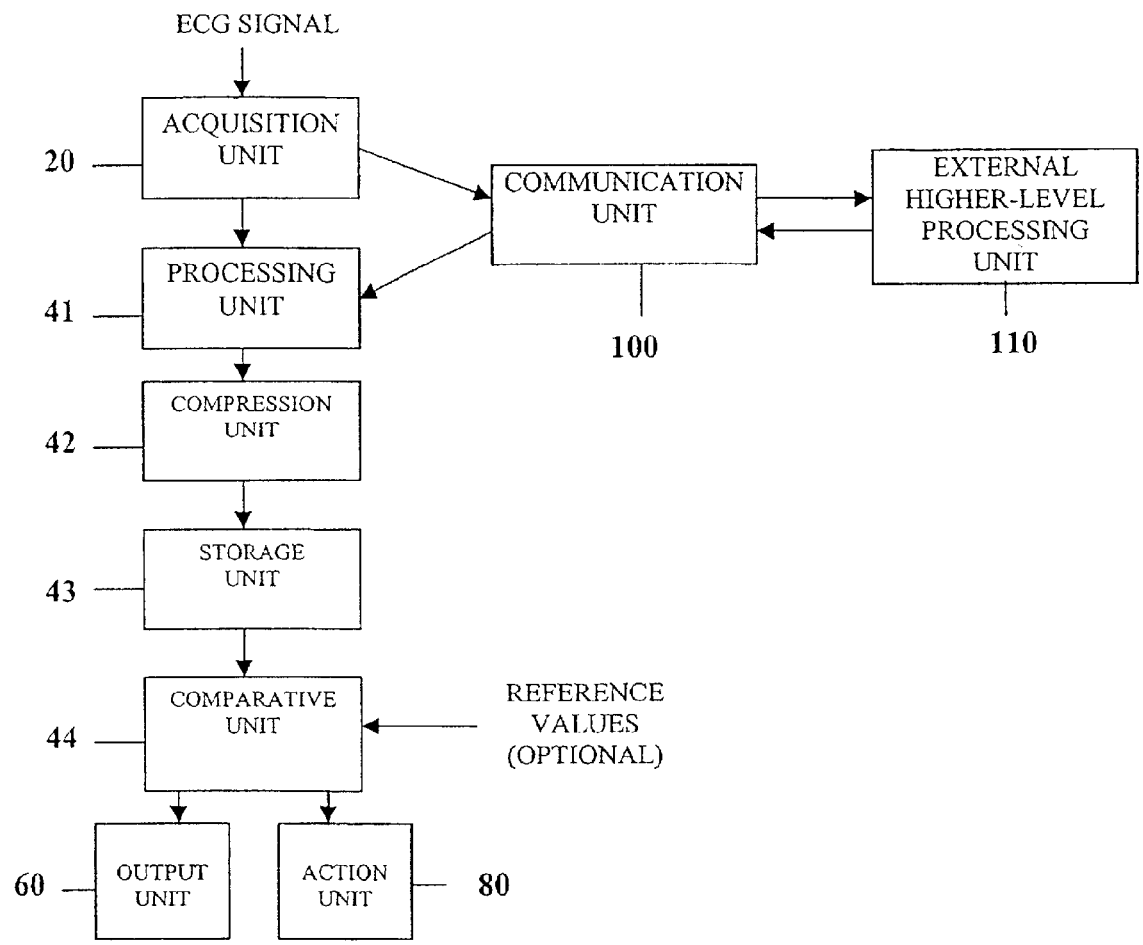
FIG. 5 is a flowchart of operation of the preferred embodiment.

FIG. 5 is a flow-chart of operation of this medical device.

Figure 6:
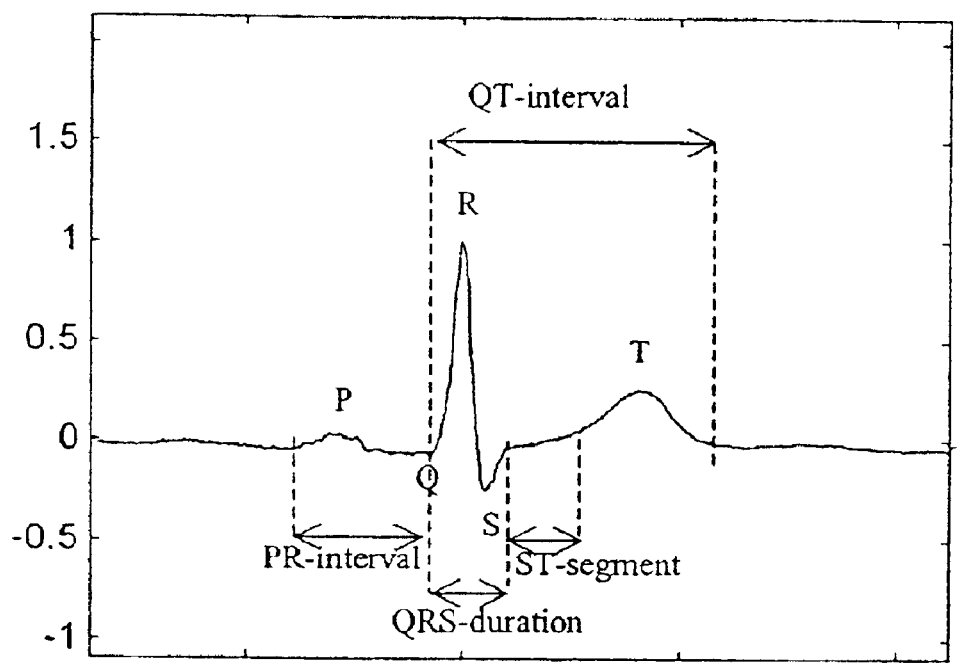
FIG. 6 is a graph of a representative electrocardiogram from a normal subject and its segmentation into a plurality of characteristic points and segments.

FIG. 6 shows a representative ECG obtained from a normal subject and position of the characteristic points in the signal.

To achieve the optimal sensitivity in the detection of hidden or small ECG changes, a pattern recognition approach is used that extracts the basis functions from the statistics of the signal itself and gives the least error representation of the signal. Specifically, a principal component analysis (PCA) is applied which requires a minimum number of basis functions to obtain a fixed reconstruction error compared to other orthogonal expansions.

PCA is an orthogonal transformation that employs a weighted combination of several basis functions to represent a signal. The basis functions are fixed, whereas PCA-coefficients vary as a function of time. The choice of PCA for detection and characterization of the changes in ECG-signal was related to the following properties of the transform:

minimization of the mean square error within a finite number of basis functions guarantees that no other expansion will give a lower approximation error (with respect to the mean square error).

clustering transformational properties with minimization of the entropy in terms of the average squared coefficients used in the expansion.

In contrast to the methods that use fixed-form basis functions (for example, Fourier representation), basis functions in PCA are derived from the statistics of the signal. Therefore, PCA with the same number of basis functions provides a smaller residual error than other expansions.

Assume that the pattern contains M vectors $x_i$, i=1,2, . . . , M, and the length of each vector is equal to N points. To obtain the PCA coefficients, the matrix $C_x$ must be obtained using the average of the covariance matrices of x vectors. The matrix $C_x$ is defined as $$C_x = E\{(x-m_x)(x-m_x)^T\} \quad (1)$$

where $$m_x = E\{x\} \quad (2)$$

is the mean vector, and E corresponds to the expected value. Assume that the pattern of the time series has M unit-length vectors $x_i$, i=1,2, . . . , M, and the length of each vector is equal to N points, to generate a matrix $C_x$ from the outer products of vectors x. A matrix $C_x$ of M vectors $x_i$ can be calculated as $$C_x \cong \frac{1}{M} \sum_{i=1}^{M} \{(x_i - m_x)(x_i - m_x)^T\}, \quad (3)$$

where $i = 1, 2, \ldots M$, and $$m_x \cong \frac{1}{M} \sum_{i=1}^{M} x_i \quad (4)$$

From the matrix $C_x$ one can obtain eigenvectors $\psi_i$, i=1, 2, . . . , N and corresponding eigenvalues $\lambda_i$, i=1,2, . . . , N. Let A be the transformation matrix whose rows are the eigenvectors of $C_x$. First eigenvector corresponds to the first eigenvalue, second one corresponds to the second eigenvalue and so on. Eigenvalues are arranged in decreasing order so that $\lambda_1 \geq \lambda_2 \geq \ldots \geq \lambda_N$. Then, PCA consists of a multiplication of the transformation matrix A by vector $(x-m_x)$:

$$y = A(x-m_x) \quad (5)$$

where y is a PCA coefficient vector. If matrix A is formed by K eigenvectors that correspond to the largest eigenvalues, y is a K×1 vector. Then, the first K coefficients contain almost entire information about the signal allowing substantial reduction in the number of analyzed coefficients and thus compression of the data. In this application, PCA is applied to the time series of each primary element, that is the intervals between the cardiac beats, duration of PQ, QRS, and QT-intervals, amplitudes of P-, Q-, R-, S-, and T-waves. For instance, to determine the characteristic pattern of the series of QT-intervals from the serial ECGs, assume that the pattern consists of M unit-length vectors $x_i$. Therefore, the series is divided into M constant-length time windows to obtain vectors $x_i$. Alternatively, the unit-length vectors $x_i$ may be comprised of a combination of all or some primary elements to determine a typical combinatorial pattern of the primary elements. Still another possibility is an extension of the concept of the unit-length vectors $x_i$ into two dimensions to represent both the combined pattern of all primary elements (in the first dimension) and the serial changes of each primary element (in the second dimension). Then PCA analysis is performed as described above.

Applications of the Principal Component Analysis at Scale II and Scale III of the System In previous works, PCA was applied for detection and classification of cardiac waveforms (QRS-complexes and ST-segments) in ECG. The optimal basis functions for QRS or ST waveforms were obtained from large training sets. PCA coefficients were used to compare individual waveforms with the set of templates and to assign the waveform to one of the classes.

Instead of applying PCA to the signal as in the previous art studies, this invention preferably applies PCA to the time series of primary elements that are extracted from the ECG-signal. This modification provides the following advantages. First, this provides an objective and accurate estimation of the serial changes in the ECG-signals and reveals small or hidden abnormalities that cannot be exposed by the previously used techniques. Second, this allows dramatic compression of the data. Third, this analysis reveals independent changes in each primary element when simultaneous changes occur in several elements. The prior art analysis of the original ECG signal might not show any changes because of the cancellation effects between the elements undergoing changes in opposite directions.

Because the time series of primary elements is nonstationary and highly variable among subjects and in the same subject over different periods of time, typical waveforms or templates of this series cannot be determined. Therefore, temporal, adaptive changes in PCA coefficients are used to detect and characterize the changes in this series. Pronounced and complex changes in the series of primary elements are identified by the simultaneous changes in several PCA coefficients. Since the basis functions in this expansion are orthogonal, simultaneous changes in several coefficients represent complex disturbances in linearly independent components of the signal. These combined changes in PCA coefficients reveal serious instabilities in the cardiac function as shown in the following examples.

The signal is separated into consecutive windows, and an array of vectors is obtained from the series. A covariance matrix is formed by the formula (3), where M is the number of vectors, $x_i$ is $i^{th}$ vector, and $m_x$ is calculated as in formula (4). Basis functions or eigenvectors are obtained from this matrix. Since only one covariance N×N matrix (N is the window length) is generated from the signal, all eigenvectors are fixed.

In addition to the changes in the PCA-coefficients, changes in the basis vectors (eigenvectors) can be used to evaluate the changes in ECG and its variables and/or other physiological data at different scales. Furthermore, if the set of eigenvectors is fixed, changes in their energy (eigenvalues) can also be used for estimation of the changes in the signal and the parameters derived from the signal at different resolutions. In particular, at the low resolution scale, the analysis could be limited to the estimation of changes in the spectral characteristics of a few, most significant eigenvectors and the corresponding eigenvalues. At the higher-resolution scales, the analysis may include a greater number of studied eigenvectors and eigenvalues, and estimation of their combined changes.

EXAMPLE

The following example illustrates the sequence of ECG analysis at the system's Scales I, II and III. Serial ECG recordings from a patient A who had a structural heart disease and dynamic changes in the electrocardiogram were processed at each Scale with a different degree of detail. Scale I revealed the changes in a small number of important, primary elements using minimum computational resources. Scale II exposed changes in the primary elements that occurred in serial recordings over time. Scale III provided complete description of the serial ECG changes using a complete set of primary elements and their combinations.

Figure 7:
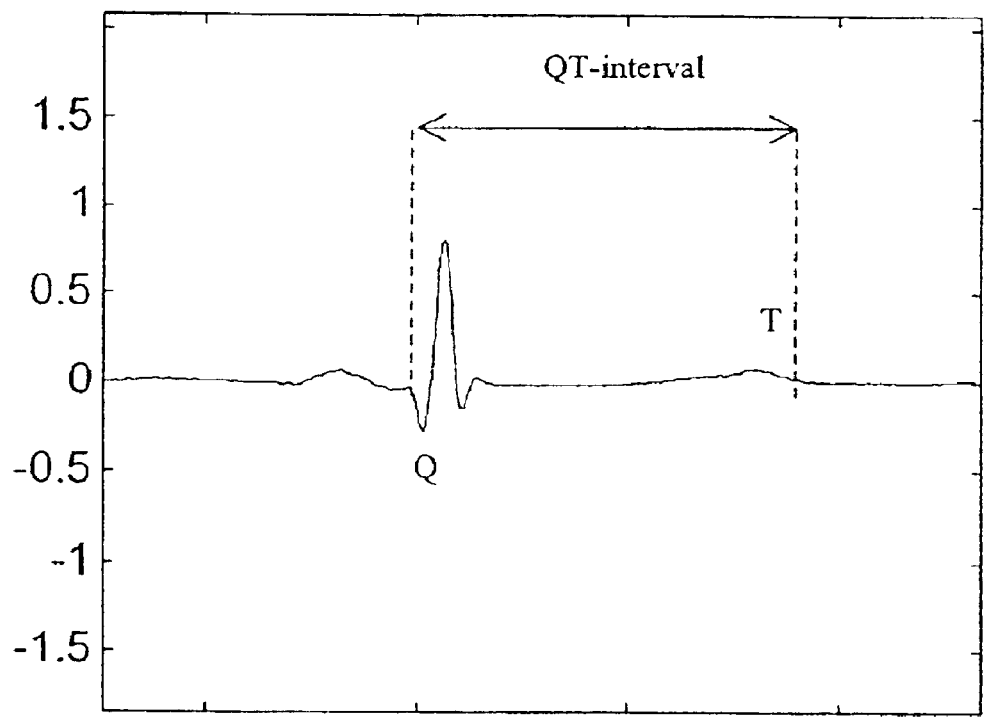
FIG. 7 is a graph of a representative electrocardiogram from a patient with a cardiac disease, large Q-wave, and prolonged QT-interval (0.5 sec) compared to the normal ECG shown in FIG. 6.

System initialization. When the system is used for the first time, initialization is required for verification and individual adjustment of the analysis criteria including identification of the primary elements and their search criteria. System initialization is performed using the hardware and software resources of the intermediate resolution Scale II and high resolution Scale III. In the initialization mode, the Scale I device transmits ECG to the higher Scale of the system via a direct or a wireless (telemetry or infrared) link. The ECG and the position of primary elements and their characteristic points (onset, peak, and offset) are visualized on a display, for example LCD display, as shown in FIG. 6. The position of characteristic points can be verified and manually edited by a user, a lay person or a medical professional. A simple manual or a software tutoring program of the typical ECG patterns, the primary elements and their characteristic points is provided for a lay person. FIG. 7 shows an ECG with a long QT-interval (0.5 sec) and a low-amplitude T-wave compared to the normal ECG shown in FIG. 6. The offset of this low-amplitude T-wave is difficult to detect automatically and a manual verification and correction are desired to ensure the accuracy. A user may also modify the set of monitored primary elements to account for a specific cardiovascular abnormality. Some of the elements may be combined into a single monitoring index, for example, a combined integral of T and U peaks can be useful for patients with possible electrolyte abnormalities.

After finishing manual verification and editing, the system automatically adjusts the search criteria for each characteristic point which include the time window, the amplitude, integral and derivative thresholds. The individually adjusted program is generated for a particular person and is automatically sent to re-program the processing sub-unit of Scale I. After the initialization, the Scale I device can work in autonomous regime without permanent connection to the higher-level Scales.

Re-initialization and serial adjustment can be performed to modify the set of primary elements and indexes and their search criteria. In addition to the procedure that was described in the system initialization, the results of the Scale II analysis can be used for serial adjustment. In particular, the primary elements and indexes whose time series and PCA coefficients demonstrate unstable behavior can be identified and included into the Scale I analysis.

Figures 8, 9:
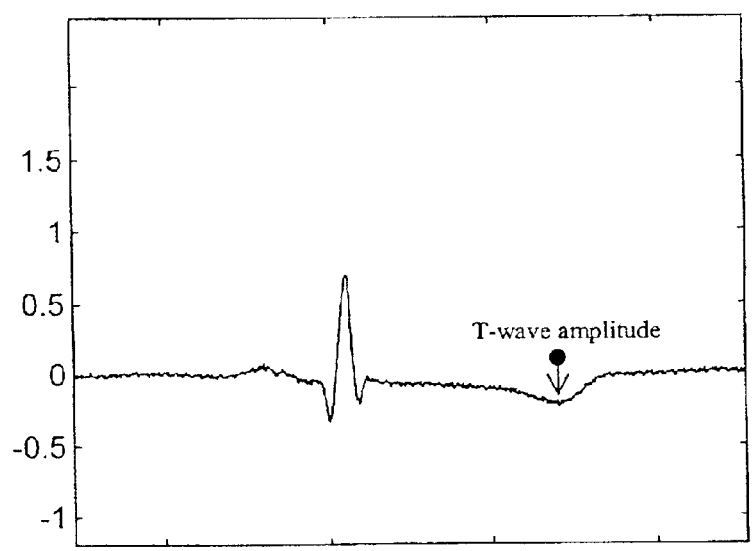
FIG. 8 shows the readings from the output indicators at Scale I in the static mode for the abnormal ECG in FIG. 6 (N denotes normal value, A denotes abnormal value of a characteristic parameter compared to default values).
FIG. 9 is a graph of ECG obtained from the same patient as in FIG. 8 several hours later. The amplitude of T-wave decreased by 0.3 mV compared to the previous recording shown in FIG. 7.

Scale I. FIG. 7 is a graph of a representative electrocardiogram which has large Q-wave, and prolonged QT-interval. These abnormalities have been detected by the method of the present invention at the Scale I and represented qualitatively as abnormal findings and quantitatively as the exact magnitude of changes compared to the default values as shown in FIG. 8 which are readings of output indicators at Scale I for abnormal (A) and normal (N) ECG in the static mode. FIG. 9 is a graph of ECG obtained from the same patient several hours later. The amplitude of T-wave decreased by 0.3 mV compared to the previous recording shown in FIG. 8. The amplitude of T-wave decreased by 0.3 mV compared to the previous recording shown in FIG. 7. FIG. 9 shows the readings from the output indicators that represent the changes (C) in this ECG compared to the previous one.

Figure 11:
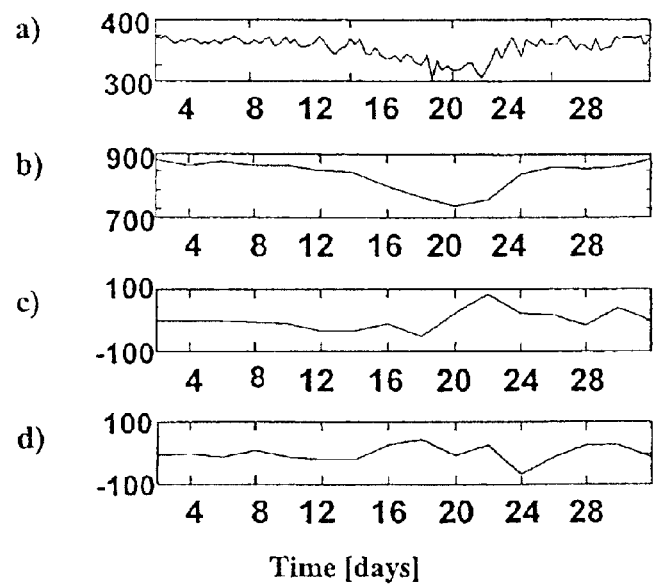
FIG. 11 shows the time series of QT-intervals (panel A) and its first three PCA-coefficients (panels B–D) in patient A during one month.
Figure 12:
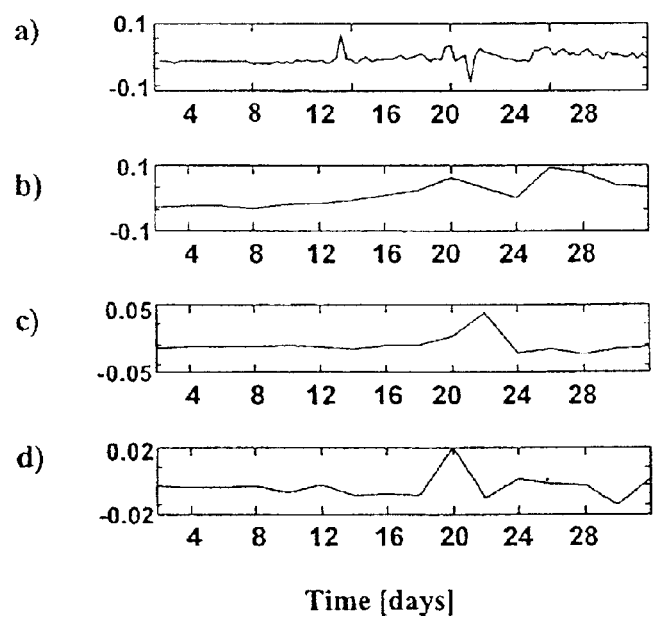
FIG. 12 shows the time series of T-wave amplitudes (panel A) and its first three PCA-coefficients (panels B–D) in patient A during one month.

Scale II. Serial ECGs have been obtained from patient A. and processed by means of Scale II to expose the time course of the serial changes that occurred in the this patient over a period of 1 month. FIG. 11, panel a, represents the series of QT-intervals that were extracted from these recordings; panels b–d demonstrate the changes in the first three PCA-coefficients that were obtained from this signal. At the end of the last recording, the patient developed a life-threatening disorder of cardiac function. However, this method reveals instability in the cardiac function as early as 20 days before the event when all known physiological indicators remain normal. FIG. 12 demonstrates changes in the T-wave amplitude extracted from the same recordings (panel a) and the corresponding first three PCA-coefficients. The time series are complex and the changes cannot be easily described or analyzed by simple tools, therefore, the changes in the signal are analyzed in a compressed form using the series of the first three PCA-coefficients which contain the most significant information about the signal. The ECG was relatively stable during the first 10 days but then became unstable as reflected by variations in the PCA-coefficients. The patient suffered a life-threatening cardiac disorder at the end of the month. However, variations in the PCA-coefficients were observed long before the event, when all physiological indicators remained normal. Calculating the changes in the variance of the PCA coefficients provides an accurate estimation of the changes and stability of the series. Unlike linear estimators such as the mean and variance of the signal or nonlinear estimators such as fractal scaling exponent or correlation dimension, disturbances in the PCA coefficients are indicative of any changes in the pattern of the signal. Therefore, analysis of PCA coefficients reveals both linear and nonlinear changes in the signal.

Figure 13:
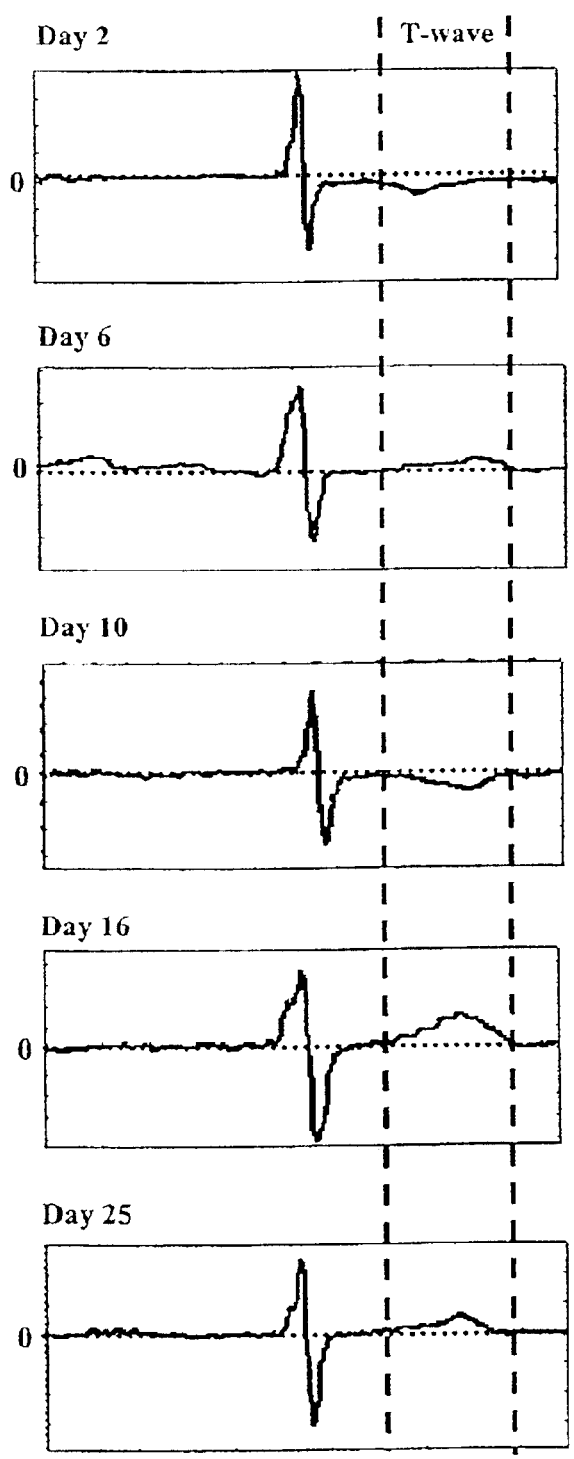
FIG. 13 shows serial ECG tracings of patient A during one month.

Scale III. The same ECGs that were analyzed at the Scales I and II, were further processed by means of Scale III to expose the entire dynamics of the ECG signal. FIG. 13 demonstrates the ECG waveforms that were obtained from serial ECG recordings in patient A. Since all the data points are included into the analysis, the changes in the shape and polarity of T-wave can be easily detected in the serial ECGs using visual inspection, PCA or other signal processing tools. The polarity of the T-waves are negative in days 2 and 10 recordings, and are positive in days 6, 16 and 25 recordings.

Figure 14:
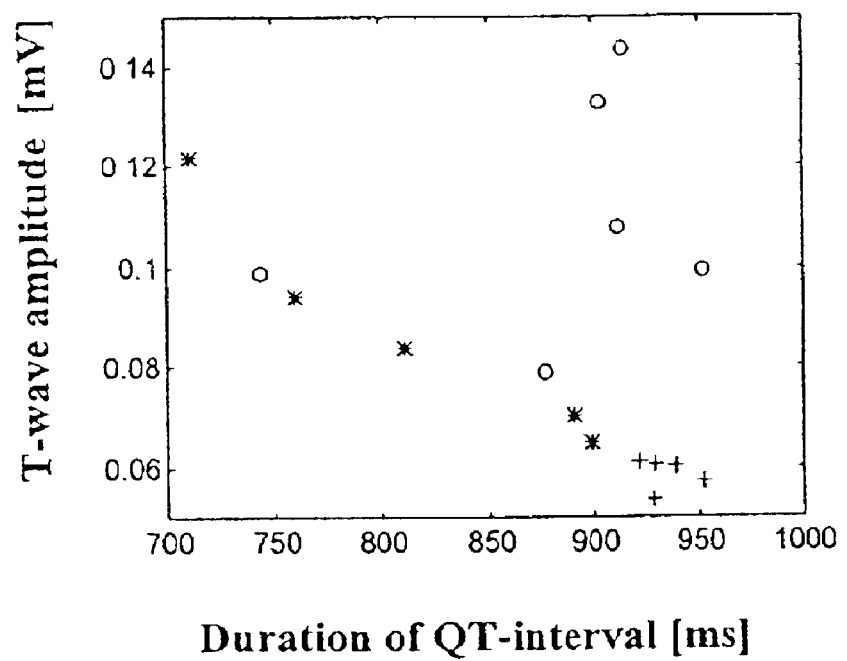
FIG. 14 is a plot of the first PCA-coefficient obtained from the series of QT-intervals versus the first PCA-coefficient obtained from the series of T-wave amplitudes in patient A.

FIG. 14 shows the changes in the PCA coefficients of these series in Scale III, dynamics of ECG in patient A in a space of the first, most significant PCA-coefficients. Y-axis represents the first PCA-coefficient that was obtained from T-wave amplitude. X-axis represents the first PCA-coefficient that was obtained from QT-interval. Each point corresponds to one-hour value. Values during 1–5 days are marked as pluses, values during 6–10 days are marked by stars, values during 11–16 days are marked by circles. Higher dispersion and change in the location of the points during 6–16 days compared to the first five days indicates instability of serial ECGs. A small cluster of data points in the lower right corner of the figure corresponds to the unchanged signals during the first 5 days of the recording. Then, the dispersion of the points increases and their location changes which reflects increased instability of the signals. Thus, the combined changes in the coefficients that were obtained from different primary elements revealed instability in the cardiac activity that preceded aggravation of the cardiac disease.

In addition to the above-described orthogonal linear decomposition, other multidimensional scaling based on non-metric distances and mapping techniques can be used for multi-scale ECG analysis. These include but are not limited to non-orthogonal linear mappings, nonlinear mappings and other projection methods, that make use of such mathematical tools as the domain and range straightening, and re-scaling (change of variables). In addition, other statistical estimators, such as analysis of variance, cluster analysis, factor analysis, canonical analysis, regression and discriminant function analysis, and probabilistic methods, such as Bayesian probability, can be applied for estimating the temporal changes in the physiological data and in the derived variables at different scales (resolutions). In particular, Mahalanobis distance, a measure of distance between two points in the space defined by two or more, possibly, correlated variables can be used to determine the probability of a change in the physiological data at different scales. For each variable, the location of the point mean steady-state value (centroid 1) and the mean unsteady value (centroid 2) are determined. Mahalanobis distances from the steady-state and the unsteady centroids to each data point are then calculated. The probability that a point belongs to the steady-state or the unsteady sector is proportional to the Mahalanobis distance from that sector centroid. These distances, for example, could be used for the estimatation of temporal changes in electrocardiographic T-wave amplitude shown in FIG. 13. In particular, the probability of a change in the new T-wave amplitude data at a low-resolution scale can be determined using Mahalanobis distance between the new data and the two centroids (steady-state and unsteady one). At the higher-resolution scale, the probability of a change, its magnitude, and other characteristics could be estimated more precisely by separating the steady-state and the unsteady sectors into sub-sectors, determining the corresponding centroids, and estimating Mahalanobis distances between the new data and the centroid of each sub-sector. The locations of the centroids are updated after the new data are collected to provide time-adjusted, individual reference values. The distances between the centroids demonstrate the individual range of variations in the studied variables, which can be compared to the average values in a group or a population. Mahalanobis distances can also be used to estimate the changes in combinations of variables.

This procedure is similar to the inclusion of additional dimensions (components) into the PCA. However, unlike PCA, the nonlinear estimation is not limited to orthogonal components and metric distances, but may include non-orthogonal components and nonlinear estimators.

It is therefore seen that this invention provides an ECG and/or other physiological data analysis system and method for detecting a plurality of primary elements in an ECG signal, and comparing the detected signals with reference values both quantitatively and qualitatively. The outputs from the system in both low level resolution and higher levels of resolution can be understood by both lay persons and medical professionals. The system includes means for exchanging information and direction from an external computer for analysis and modification of the low resolution analysis of the signal.

Whereas particular aspects of the method of the present invention and particular embodiments of the invention have been described for purposes of illustration, it will be appreciated by those skilled in the art that numerous variations of the details may be made without departing from the invention as described in the appended claims.

What is claimed is:

1. A method for analysis of physiological or health data in at least two levels of detail, said method comprising:

analyzing a plurality of primary elements in said data in first scale, low level resolution to detect one-time changes in such primary elements and thereby identify abnormal or unstable primary elements;

comparing said primary elements with reference values for such primary elements, and representing deviation of primary elements from the reference values in a form understandable to a lay person;

analyzing at least some of the same said primary elements in said data in second scale, higher level resolution using mathematical decomposition to provide detailed characterization of serial changes in said abnormal or unstable primary elements; and exchanging information between said analyzing in said first and second levels of resolution to improve at least one of said first and second analyses.

2. A method as set forth in claim 1 in which said analyzing in a second scale, higher level resolution uses orthogonal mathematical decomposition.

3. A method as set forth in claim 2 in which said analyzing in said second scale, higher resolution further includes:

combining a plurality of said serial changes in the abnormal or unstable primary elements and analyzing the combined changes using orthogonal mathematical decomposition; and selecting a combination of parameters for tracking the changes in said abnormal or unstable elements and sending information respecting the selected combination to said low-resolution analysis for adjustment of monitoring parameters.

4. A method as set forth in claim 2 in which said analyzing in said second scale, higher resolution comprises:

forming a time series from said serial changes;

characterizing said time series using Principal Component Analysis (PCA) and generating PCA-coefficients indicative of both linear and nonlinear changes in the individual pattern; and determining the magnitude of said linear and nonlinear changes by using time varying mean and variance of said PCA-coefficients and determining the complexity of said linear and nonlinear changes by calculating the number of PCA-coefficients that exhibit substantially simultaneous changes.

5. A method as set forth in claim 2 in which said analyzing in said second scale, higher resolution comprises:

forming time series from said serial changes;

characterizing said time series using Principal Component Analysis (PCA) and generating PCA-coefficients indicative of both linear and nonlinear changes in the individual pattern;

presenting said PCA-coefficients as a vector in n-dimensional space wherein n is the number of variables analyzed; and determining the magnitude and direction of the combined changes in the characteristic variables by the changes in the magnitude and direction of said n-dimensional vector.

6. A method as set forth in claim 2 which includes adjusting said analyzing in low resolution based on said detailed characterization of serial changes in the primary elements.

7. A method as set forth in claim 6 that further comprises representing deviations of said primary elements from said reference values in a quantitative form for use by a medical professional.

8. A method as set forth in claim 2 which includes producing a visual or audio warning signal when said low resolution detects an abnormal or unstable primary element.

9. A method as set forth in claim 2, in which the multi-resolution analysis and representation are applied for improved detection of changes during one-time examination, assessment of short-term and long term dynamics, which include fitness level, disease progression, treatment, complications and side-effects control, physical examination, early detection of subtle changes, and timely initiation or adjustment of therapy, early prediction and prevention of physiological disorders and abnormalities, comparison of the values of data obtained from individual patients against averages of values obtained from a group of patients or population of patients to facilitate analysis of individual data and to determine the values that characterize groups of patients with similar characteristics and/or similar disorders.

10. A method as set forth in claim 1 in which orthogonal mathematical decomposition is applied to both said resolution scales.

11. A method as set forth in claim 1 in which the changes in basis vectors (eigenvectors) are used to evaluate the changes and variables in the data at both resolution scales.

12. A method as set forth in claim 11 in which changes in said eigenvalues are used for estimation of the changes in the variables in the data at both resolution scales so that at the low resolution scale, the analysis is limited to the estimation of changes in the spectral characteristics of a few, most significant eigenvectors and the corresponding eigenvalues, and at the higher resolution scales, the analysis includes a greater number of studied eigenvectors and eigenvalues, and estimation of their combined changes.

13. A method as set forth in claim 1 in which analyzing said data in low and higher resolution to provide detailed characterization of serial changes in said abnormal or unstable primary elements is performed using at least one method selected from the following: multidimensional scaling non-metric distances, mapping techniques, non-orthogonal linear mappings, nonlinear mappings, projection methods, statistical estimators, analysis of variance, cluster analysis, factor analysis, canonical analysis, regression and discriminant function analyses, probabilistic methods, Bayesian probability and Mahalanobis distance.

14. A method as set forth in claim 1, in which the multi-resolution analysis and representation are applied to other physiological signals selected from at least one of the following signals: blood pressure, cardiac output, vascular activity, temperature, respiration, cardiac, abdominal, or breathing sounds, blood flow, hormonal concentration, neural activity, electroencephalographic activity, and other electrical, mechanic, sonic, biochemical, biophysical processes in the human body, and/or demographic, psychological, or environmental data.

15. A system for detection of serial changes in physiological or health data and analysis in at least two levels of detail for use by both lay persons and medical professionals, said system comprising:

an acquisition unit for collecting physiological or health data from a subject over a period of at least several seconds;

a first analysis and processing unit for detecting a plurality of primary elements from said data and processing said primary elements in low level resolution to generate data respecting time intervals or amplitudes of said primary elements, storing reference values of said plurality of primary elements, and comparing said reference values with data newly received by said first analysis and processing unit and producing qualitative indicators and quantitative data of differences between said recorded data and said newly received data;

an output unit for displaying said qualitative indicators in a form understandable by lay persons and quantitative data for medical professionals; and a communications unit for sending quantitative data of said primary elements to a second analysis unit for processing and detailed analysis of serial changes in at least some of the same said primary elements in said data, said second analysis unit using a higher scale of resolution using mathematical decomposition for assessing small changes in serial data and for exchanging information with said first analysis and processing unit to improve at least one of said low level or higher level resolution.

16. A system as set forth in claim 15 in which said second analysis uses orthogonal mathematical decomposition.

17. A system for detection and analysis as set forth in claim 16 in which said second analysis unit characterizes time series of at least one primary element or index in said set of primary elements and indexes using Principal Component Analysis (PCA) and generating PCA coefficients indicative of both linear and nonlinear changes in the individual pattern;

determines the magnitude of said changes in the characteristic variables by using time varying mean and variance of said PCA coefficients and determining the complexity of said changes by calculating the number of PCA coefficients that exhibit substantially simultaneous changes;

presents said combination of PCA coefficients as a vector in n-dimensional space wherein n is the number of variables analyzed; and determines the magnitude and complexity of the changes in the combination of the characteristic variables by the changes in said n-dimensional vector.

18. A detection and analysis system as set forth in claim 16 in which said first analysis unit includes means for receiving commands from said second analysis unit to adjust the primary elements to be detected from said data.

19. A detection and analysis system as set forth in claim 16 in which said output unit for qualitative representation includes a static screen for one-time presentation and a dynamic screen for presenting changes in serial recordings.

20. A detection and analysis system as set forth in claim 16 in which said set of primary elements includes a complete set of characteristic fragments of ECG signals and their parameters, said set of characteristic fragments including P, Q, R, S, T and U waves, ST-segment, PR, QRS and QT-intervals, said parameters including the amplitude and duration of said waves and segments, and the time intervals between the heart beats.

21. A detection and analysis system as set forth in claim 15 in which said first and second analysis units use changes in basis vectors (eigenvectors) to evaluate the changes and variables in the data in both levels of resolution.

22. A detection and analysis system as set forth in claim 21 in which changes in said eigenvectors are used for estimation of the changes in the variables in the data at both resolution scales so that, at the low resolution scale, the analysis is limited to the estimation of the changes in the spectral characteristics of a few, most significant eigenvectors and the corresponding eigenvalues, and at the higher resolution scale, the analysis includes a greater number of studied eigenvectors and eigenvalues, and estimation of their combined changes.

23. A detection and analysis system as set forth in claim 15 in which said first and second analysis units analyze said data in low and higher resolution respectively to provide detailed characterization of serial changes in said abnormal or unstable primary elements using at least one method selected from the following: multidimensional scaling, non-metric distances, mapping techniques, non-orthogonal linear mappings, nonlinear mappings, projection methods, statistical estimators, analysis of variance, cluster analysis, factor analysis, canonical analysis, regression and discriminant function analyses, probabilistic methods, Bayesian probability and Mahalanobis distance.

24. A detection and analysis system as set forth in claim 15 in which said first and second analysis units analyze other physiological data selected from at least one of the following signals: blood pressure, cardiac output, vascular activity, temperature, respiration, cardiac, abdominal, or breathing sounds, blood flow, hormonal concentration, neural activity, electroencephalographic activity, and other electrical, mechanic, sonic, biochemical, biophysical processes in the human body and/or demographic, psychological, or environmental data.

25. A detection and analysis system as set forth in claim 15 in which said output unit includes a screen for displaying said qualitative indicators of a minimal set of most significant indexes to indicate a substantially abnormal physiological or health data and a screen for quantitative representation that represents a complete set of characteristic fragments and their parameters.

26. A detection and analysis system as set forth in claim 15 in which said first analysis and processing unit includes means for decomposing physiological or health data into a plurality of elements, and said decomposing means performs an orthogonal decomposition to extract the most significant information about said physiological or health data.

27. A detection and analysis system as set forth in claim 15 in which said first analysis and processing unit, output unit and communications unit are combined in one pocket size unit connected to said communication unit.

28. A detection and analysis system as set forth in claim 15 in which said communication unit is wireless.

29. A detection and analysis system as set forth in claim 15 in which said first analysis and processing unit includes storage for a physiologic range of the primary elements and detector of error and noise to reject the data upon detection of the primary elements or the indexes beyond the physiologic range.

30. A detection and analysis system as set forth in claim 15 in which said output unit includes a display for viewing the physiological data.

31. A portable system for monitoring physiological or health data and analyzing the data in at least two levels of detail (or resolution) for displaying changes detected in the data, said portable system comprising:
   an acquisition unit for receiving physiological or health data generated by monitoring a subject for at least several seconds;
   at least one analysis unit for detecting a plurality of primary elements from said signals to detect one-time changes in such primary elements and thereby identify abnormal or unstable primary elements, storing said plurality of primary elements, comparing said plurality of primary elements which have been stored with a plurality of primary elements newly received from said analysis nodule and producing both qualitative and quantitative information representing the differences in the data in low level resolution, and using mathematical decomposition to provide detailed characterization of serial changes in said abnormal or unstable primary elements in higher level resolution;
   an output unit for displaying qualitative information understandable by lay persons and quantitative information useful to medical professionals; and
   a communications unit for sending data to a remote processing unit for analysis by medical professionals and exchanging information between said at least one analysis unit and said remote processing unit to improve functionality of at least one of said one analysis unit and said remote processing unit.

32. A portable system as set forth in claim 31 which forms a time series from said serial changes, characterizes said time series using Principal Component Analysis (PCA) and generates PCA-coefficients indicative of both linear and nonlinear changes in the individual pattern, determines the magnitude of said linear and nonlinear changes by using time varying mean and variance of said PCA-coefficients and determines the complexity of said linear and nonlinear changes by calculating the number of PCA-coefficients that exhibit substantially simultaneous changes.

33. A portable system as set forth in claim 31 which includes means for adjusting said characterization in low level resolution based on characterization of the serial changes in high level resolution.

34. A portable system as set forth in claim 31 that further includes an analysis unit for analyzing said primary elements in third level high resolution using orthogonal mathematical decomposition to provide more detailed characterization of serial changes in the abnormal or unstable primary elements.

35. A portable system as set forth in claim 31 in which said set of primary elements includes a complete set of characteristic fragments of ECG signals and their parameters, said set of characteristic fragments including P, Q, R, S, T and U waves, ST segment, PR, QRS and QT intervals, and said parameters including the amplitude and duration of said waves and segments, and the time intervals between heart beats.

36. A portable system as set forth in claim 31 in which said output unit includes a display for the physiological or health data.

37. A portable system as set forth in claim 31 in which said first and second analysis units use changes in basis vectors (eigenvectors) to evaluate the changes and variables in the data in both levels of resolution.

38. A portable system as set forth in claim 37 in which changes in said eigenvectors are used for estimation of the changes in the variables in the data at both resolution scales so that, at the low resolution scale, the analysis is limited to the estimation of the changes in the spectral characteristics of a few, most significant eigenvectors and the corresponding eigenvalues, and at the higher resolution scale, the analysis includes a greater number of studied eigenvectors and eigenvalues, and estimation of their combined changes.

39. A portable system as set forth in claim 31 in which said first and second analysis units analyze said data in low and higher resolution respectively to provide detailed characterization of serial changes in said abnormal or unstable primary elements using at least one method selected form the following: multidimensional scaling, non-metric distances, mapping techniques, non-orthogonal linear mappings, nonlinear mappings projection methods, statistical estimators, analysis of variance, cluster analysis, factor analysis, canonical analysis, regression and discriminant function analyses, probabilistic methods, Bayesian probability and Mahalanobis distance.

40. A portable system as set forth in claim 31 in which said first and second analysis units analyze other physiological data selected from at least one of the following signals: blood pressure, cardiac output, vascular activity, temperature, respiration, cardiac, abdominal, or breathing sounds, blood flow, hormonal concentration, neural activity, electroencephalographic activity, and other electrical, mechanic, sonic, biochemical, biophysical processes in the human body and/or demographic, psychological, or environmental data.

41. A system for detection of serial changes in health data and analysis of the data for use by both lay persons and medical professionals, said system comprising:
   an acquisition unit for collecting health data from a subject over a peirod of at least several seconds;
   an analysis unit for detecting a plurality of primary elements from said data and processing said primary elements to generate references values respecting said primary elements, storing said references values, and comparing said reference values with data newly received by said analysis and processing unit usign mathematical decomposition and producing qualitative and quantitative data of differences between said reference data and said newly received data; and
   an output unit for displaying said quantitative and qualitative data.

42. A system as set forth in claim 41 in which said mathematical decomposition is linear orthogonal.

43. A system as set forth in claim 41 in which said mathemetical decomposition is linear non-orthogonal.

44. A system as set forth in claim 41 in which said mathematical decomposition is nonlinear.

45. A system as set forth in claim 41 which includes a communications unit for sending data from said analysis unit to a second analysis unit for processing and detailed analysis of serial changes in at least some of the same primary elements in said data.

46. A method for detecting serial changes in health data and analysis of the data for use by both lay persons and medical professionals, said system comprising:
    collecting health data from a subject over a period of at least several seconds;
    analyzing said health data to detect a plurality of primary elements in said data and processing said primary elements to generate reference values respecting said primary elements, storing said reference values, and comparing said reference values with data newly received by said analysis and processing unit using mathematical decomposition and producing qualitative and quantitative data of differences between said reference data and said newly received data; and
    displaying said quantitative and qualitative data.

47. A method as set forth in claim 46 in which said mathematical decomposition is linear orthogonal.

48. A method as set forth in claim 46 in which said mathematical decomposition is linear non-orthogonal.

49. A method as set forth in claim 46 in which said mathematical decomposition is nonlinear.

50. A method as set forth in claim 46 which includes transmitting said quantitative data to a remote analysis unit and processing system for processing and detailed analysis of serial changes in at least some of the same primary elements in said data.

51. A system for detection of serial changes in health data and analysis of the data, said system comprising:
    an implantable acquisition unit for collecting health data from a subject; and
    an external processing unit in wireless communication with said implantable acquisition unit;
    wherein at least one of said implantable acquisition unit and said external device having the capability of detecting a plurality of primary elements from said data and processing said primary elements to generate reference values respecting said primary elements, storing said reference values, comparing said reference values with data newly received by said implantable acquisition unit using mathematical decomposition to generate health data of differences between said reference data and said newly received data.

52. A system as set forth in claim 51 in which said external processing unit is selected from a personal computer, a specialized processor and a computer organizer.

53. A system as set forth in claim 52 in which said external processing unit has a wireless bi-directional communication with said acquisition device and with a remote server.

54. A system as set forth in claim 52 in which said external processing unit has a display for showing health information.

55. A system as set forth in claim 52 in which said external processing unit has a function for manual input of data.

56. A system as set forth in claim 51 in which said acquisition device includes means for receiving commands from said external processing device to adjust the primary elements to be detected.

57. A system as set forth in claim 51 in which said mathematical decomposition is linear orthogonal.

58. A system as set forth in claim 51 in which said mathematical decomposition is linear non-orthogonal.

59. A system as set forth in claim 51 in which said mathematical decomposition is nonlinear.

60. A system as set forth in claim 51 in which said mathematical decomposition is performed using at least one of the following methods: multidimensional scaling, non-meteric distances, mapping techniques, non-orthogonal linear mappings, non-linear mappings, projection methods, ststistical estimators, analysis of variance, cluster analysis, factor analysis, canonical analysis, regression and discriminant function analyses, probabilistic methods, Bayesian proability and Mahalanobis distance.

61. A system as set forth in claim 51 in which said acquisition unit processes said primary elements at a first level of resolution and said external processing unit processes said health data at a second higher level of resolution.

62. A system as set forth in claim 51 in which said external processing unit processes said health data at more than one higher levels of resolution.

63. A system as set forth in claim 51 in which said external processing unit consist of at least two units in communication with each other.

64. An external processing unit as set forth in claim 63 in which said communication between said at least two units is wireless.

65. A system as set forth in claim 51 in which said health data are selected from at least one of the following signals: blood pressure, cardiac output, vascular activity, temperature, respiration, cardiac, abdominal, or breathing sounds, blood flow, hormonal concentration, neural activity, electroencephalographic activity, and other electrical, mechanical, sonic, biochemical, biophysical processes in the human body and/or demographic, psychological, or enviromental data.

* * * * *